(12) United States Patent
Seri et al.

(10) Patent No.: US 12,138,358 B2
(45) Date of Patent: Nov. 12, 2024

(54) STERILIZATION METHOD USING PLASMA

(71) Applicant: ALMA MATER STUDIORUM—UNIVERSITA' DI BOLOGNA, Bologna (IT)

(72) Inventors: Paolo Seri, Civitanova Marche (IT); Gabriele Neretti, San Lazzaro di Savena (IT); Carlo Angelo Borghi, Bologna (IT)

(73) Assignee: Alma Mater Studiorum—Universita' Di Bologna, Bologna (IT)

( * ) Notice: Subject to any disclaimer, the term of this patent is extended or adjusted under 35 U.S.C. 154(b) by 179 days.

(21) Appl. No.: 16/972,025

(22) PCT Filed: Jun. 7, 2019

(86) PCT No.: PCT/IT2019/050129
§ 371 (c)(1),
(2) Date: Dec. 4, 2020

(87) PCT Pub. No.: WO2019/234781
PCT Pub. Date: Dec. 12, 2019

(65) Prior Publication Data
US 2021/0236674 A1 Aug. 5, 2021

(30) Foreign Application Priority Data
Jun. 7, 2018 (IT) .......................... 102018000006094

(51) Int. Cl.
*A61L 2/14* (2006.01)
(52) U.S. Cl.
CPC ........... *A61L 2/14* (2013.01); *A61L 2202/122* (2013.01); *A61L 2202/14* (2013.01); *A61L 2202/15* (2013.01); *A61L 2202/21* (2013.01)

(58) Field of Classification Search
CPC .. A61L 2/14; A61L 2202/122; A61L 2202/14; A61L 2202/15; A61L 2202/21
See application file for complete search history.

(56) References Cited

U.S. PATENT DOCUMENTS

| 2010/0254853 A1 | 10/2010 | Lee et al. | |
| 2011/0008207 A1* | 1/2011 | Arai | A61L 2/24 422/186.04 |

FOREIGN PATENT DOCUMENTS

EP  2275146  1/2011

OTHER PUBLICATIONS

Neretti et al. "Geometry optimization of linear and annular plasma synthetic jet actuators." 2017. J. Phys. D: Appl. Phys. 50 015210. (Year: 2016).*

* cited by examiner

*Primary Examiner* — Timothy C Cleveland
(74) *Attorney, Agent, or Firm* — BakerHostetler

(57) ABSTRACT

Sterilization method using plasma for sterilizing objects, wherein it is provided to introduce the objects to be sterilized into a sterilization chamber (13) and covey toward the latter a flow of air coming from a feed pipe (17) on which a plasma generator device (12) is disposed able to generate one or more gaseous compounds comprising a mixture of reactive oxygen species (ROS) and of reactive nitrogen species (RNS) so that the air is the carrier fluid which conveys the gaseous compounds toward the sterilization chamber (13); the method also provides to control the electric power used to produce the plasma as a function of the composition and/or the quantity of reactive species present in the sterilization chamber (13).

8 Claims, 3 Drawing Sheets

STERILIZATION METHOD USING PLASMA

CROSS-REFERENCE TO RELATED APPLICATIONS

This application is the National Stage of International Patent Application No. PCT/IT2019/050129, filed Jun. 7, 2019, which claims priority to Italian Application No. 102018000006094, filed Jun. 7, 2018, the disclosures of which are incorporated herein by reference in their entirety.

FIELD OF THE INVENTION

The present invention concerns a sterilization method using plasma for sterilizing loose or packaged objects, for example in the pharmaceutical or food sector. In particular, the invention concerns a sterilization method using non-thermal plasma, in the context of an indirect type of treatment, in which the objects to be sterilized are placed at a certain distance from the plasma.

BACKGROUND OF THE INVENTION

Sterilization methods using plasma have been known in the state of the art for a long time.

International patent application WO-A1-81/02809 describes a sterilization method using plasma for articles packaged in a porous package which allows the sterilization of the articles enclosed therein.

Sterilization apparatuses and methods using plasma are further described by patent documents WO-A2-96/21463, WO-A2-02/22180, US-A-5.288.460 and KR-A-20170016809.

The solutions known in the state of the art have various disadvantages.

One disadvantage of the sterilization methods known in the state of the art is that they are not suitable to be used on an industrial scale since they involve long and laborious procedures.

For example, document KR-A-20170016809 describes a method in which it is provided to sterilize an object contained in a flexible bag, in which it is provided to create a vacuum, where the plasma is conveyed directly. It is clear that such a solution is laborious and complex from the point of view of the plant and the procedures for its implementation, and therefore is not suitable to be used on an industrial scale.

Another disadvantage of the sterilization methods known in the state of the art is that they provide plasma generation conditions that can generate side effects on the objects to be sterilized.

For example, documents WO-A2-96/21463, WO-A2-02/22180 describe methods in which it is provided to introduce respectively water vapor and wet gas in the sterilization chamber, and then apply an adequate energy inside the chamber itself.

The humidity present in the sterilization chamber causes the disadvantage that the objects to be sterilized can suffer corrosive phenomena by the acids formed by the discharge in the presence of water vapor, in particular if they comprise metal parts.

Another disadvantage of these methods is due to the fact that the energy used to generate the plasma is applied directly in the sterilization chamber where the objects are placed, which can be subjected to very significant thermal or electromagnetic shocks, which can damage them.

Finally, document US-A-5.288.460 describes a controlled temperature sterilization method using plasma which requires an expensive and bulky apparatus. Among other things, the apparatus requires means to cool the gases to reduce their temperature, and a particular disposition of pipes able to facilitate the dissipation of the heat from the gases involved in the process.

As known in the state of the art, obtaining the plasma is influenced by many different factors. Among the main ones are the voltage applied to the electrodes, the very geometry of the electrodes, the waveform of the voltage, its value and frequency, its application time, and the composition of the starting gas.

One disadvantage of the sterilization methods using plasma known in the state of the art is that the generation of plasma is a complex and delicate step which requires adjusting the different factors mentioned above optimally, in order to obtain the desired sterilizing effect without creating conditions that can damage the objects that have to be sterilized.

In fact, it is known that the use of certain gases that are suitable to obtain the desired sterilization effect, such as for example ethylene oxide (EtO), presents considerable disadvantages.

A first disadvantage linked to the use of this gas is that it is toxic, having in particular carcinogenic effects. When sterilization is obtained using ethylene oxide, in the presence or absence of discharges, significant traces of this gas have been found on the surfaces of the sterilized objects. Consequently, its use is to be avoided as it is evident that it can be harmful to the health of people who come into contact with the objects.

Another disadvantage linked to the use of this gas is that it is highly flammable. Storing large quantities of this gas is therefore extremely dangerous, and there are considerable risks for the safety of operators working in sterilization plants. Furthermore, the correct management of this material is expensive as it has to comply with the reference standards of personal and environmental safety.

There is therefore the need to perfect the sterilization methods using plasma known in the state of the art, so as to overcome at least one of its disadvantages.

It is a purpose of the present invention to perfect a reliable sterilization method using plasma which allows to sterilize the objects effectively with sterilization cycles of reduced duration.

Another purpose of the present invention is to perfect a sterilization method using plasma able to adapt to pre-existing plants and structures, without the need to perform long, complicated and expensive structural adjustment operations.

Another purpose of the present invention is to perfect a safe sterilization method using plasma which does not provide the use of dangerous gases.

It is also a purpose of the present invention to perfect a sterilization method using plasma which is economical, both with regard to the gases used, and also with regard to the structure of an apparatus suitable to implement the method.

Another purpose of the present invention is to perfect a sterilization method using plasma which is suitable to be used in the context of sterilization processes on an industrial scale.

Another purpose of the present invention is to perfect a sterilization method using plasma which is not polluting, since no toxic or polluting gas is released into the atmosphere.

The Applicant has devised, tested and embodied the present invention to overcome the shortcomings of the state of the art and to obtain these and other purposes and advantages.

SUMMARY OF THE INVENTION

The present invention is set forth and characterized in the independent claims, while the dependent claims describe other characteristics of the invention or variants to the main inventive idea.

In accordance with the above purposes, a sterilization method using plasma is provided for sterilizing objects, comprising the following steps: introducing the objects to be sterilized in a sterilization chamber defined by a closed environment, bringing the sterilization chamber to pressures lower than atmospheric pressure, activating a plasma generator device disposed on at least one feed pipe leading into the sterilization chamber and configured to generate one or more gaseous compounds comprising a mixture of reactive oxygen species (ROS) and of reactive nitrogen species (RNS), feeding dehumidified air along the feed pipe and putting the latter in communication with the sterilization chamber so that the dehumidified air is the carrier fluid which conveys the gaseous compounds from the sterilization pipe to the sterilization chamber.

According to a characteristic aspect of the present invention, the method comprises a control step, in which it is provided to control, by means of a control unit, the electric power used to produce the plasma during the activation step of the plasma generator device, as a function of the composition and/or the quantity of reactive species present in the sterilization chamber, detected by suitable sensor means.

In one embodiment, the plasma generator device comprises one or more electrodes, disposed on walls of the feed pipe, according to a configuration able to optimize the electro-hydrodynamic effect, so as to increase the quantity of reactive species produced in the unit of time.

In one embodiment, the feed pipe has a square, circular or rectangular cross-section, and electrodes are provided on the walls of the pipe.

In one embodiment, each electrode has a circular or polygonal shape defining a configuration of symmetry with respect to central axis of symmetry.

According to embodiments described here, during the activation step of the plasma generator device, in correspondence with each electrode, a jet of the mixture of reactive species is generated which is oriented so as to develop, at least partly, coaxially to the central axis of symmetry, being directed away from the electrode, toward a longitudinal axis of development of the feed pipe, according to a direction substantially perpendicular to the latter.

In one embodiment, during the activation step, each of the electrodes is subjected to an electric field, suitably regulated during the control step, which is comprised between $10^5$ and $10^8$ volts/meter, preferably between $10^6$ and $10^7$ volts/meter.

According to some embodiments, once the activation step of the plasma generator device is terminated, a deactivation step of the latter is provided, in which it is provided to interrupt the electric power of the electrodes In one embodiment, the deactivation step provides to interrupt the flow connection between the feed pipe and the sterilization chamber and, subsequently, to wait for a deposition time during which the mixture of reactive species is deposited on the objects to be sterilized in order to perform their sterilizing function, and once the deposition time has elapsed, to remove the exhausted gases in order to remove the reactive species and the reaction products present.

In one embodiment, the exhausted gases are reintroduced into the feed pipe to be fed back to the sterilization chamber.

In another embodiment, the exhausted gases are chemically processed so as to reduce, or even eliminate, possible pollutant substances, before re-introducing them into the atmosphere.

According to another aspect of the present invention, an apparatus is provided for sterilizing objects, in particular loose objects or packaged in blisters or pouches or sachets, suitable to actuate the sterilization method using plasma mentioned above, and comprising: a closed chamber to sterilize the objects, a feed pipe to convey air toward the sterilization chamber, a plasma generator device to generate one or more gaseous compounds comprising a mixture of reactive oxygen species and reactive nitrogen species and disposed in the feed pipe, pumping members and valve units configured to control the flow of air and gaseous compounds to and from the sterilization chamber, sensor means configured to detect a quantity of the reactive oxygen species and reactive nitrogen species present inside the sterilization chamber, and a control unit configured to control at least the electric power used to produce the plasma during the activation step of the plasma generator device.

One advantage of the sterilization method using plasma according to the present invention is that it is reliable and safe, as well as economical.

Another advantage of the sterilization method according to the present invention is that it is environmentally friendly.

These advantages are mainly correlated to the fact that the method according to the present invention provides to use air as a reaction gas which cooperates with the plasma produced by the plasma generator device. Thanks to the latter, the air is substantially "activated", that is, enriched with gaseous compounds including a mixture of reactive substances, in particular of oxygen and of nitrogen.

It is evident that air is a non-polluting and absolutely economical gas, as it is freely available in large quantities.

It should be noted that these advantages also occur in the embodiments provided in accordance with variant embodiments of the present description, in which the air is not atmospheric air, but is instead the so-called "synthetic" air, that is, pre-treated air with a determinate chemical formula free of impurities and atmospheric pollutants. It is clear that in this case the method requires purchasing cylinders containing synthetic air, which is therefore not taken from the atmosphere, but this is in any case more economical than purchasing other particular gases.

Furthermore, the sterilization method according to the present invention is advantageously very safe for the safety and health of both operators and also end users. In fact, the fact that toxic gases are not used, such as for example ethylene oxide (EtO) used in many methods known in the state of the art, guarantees both the safety of the sterilization plants, and therefore of the operators who work there, and also that of the end users who will have to take and handle the sterilized objects (for example, blisters of capsules or tablets). Contrary to what typically happens in the state of the art, thanks to the fact that in the method according to the present invention toxic gases that are persistent over time are not used, there is no risk of residues of such gases, which can harm—even seriously—human health, being deposited on the sterilized objects.

Due to the fact that the sterilization method according to the present invention uses dehumidified air, another advantage is that it does not damage the objects to be sterilized by corrosive phenomena that could be triggered by the humidity present in the atmospheric air.

A further advantage of the sterilization method according to the present invention is that it can be easily implemented on an industrial scale, to sterilize, by means of sterilization cycles with a duration compatible with other working steps of the objects, large quantities of objects, possibly disposed on pallets, or other similar supports.

Another advantage of the method according to the present invention is that it has an advantageous configuration of the plasma generator device which allows to optimize the electro-hydrodynamic aspect of the flow formed by the gaseous compounds (comprising the mixture of reactive oxygen species and of reactive nitrogen species) and by the air. In this way, thanks to the conformation of the electrodes, to their corresponding disposition with respect to the feed pipe, and to the values of the electric field mentioned above to which the electrodes are subjected, it is possible to produce a greater number of reactive oxygen species and of reactive nitrogen species in the unit of time, and their transfer toward the sterilization chamber is faster and more effective.

A further advantage of the present invention is that it allows to implement the sterilization method described above by means of a simple and economical sterilization apparatus.

In fact, the sterilization apparatus according to the present invention can advantageously be easily adapted to existing plant solutions or to existing machines commonly used in the context of industrial or experimental sterilization processes, without requiring complicated and costly operations to adapt their structure.

These and other aspects, characteristics and advantages of the present disclosure will be better understood with reference to the following description, drawings and attached claims. The drawings, which are integrated and form part of the present description, show some embodiments of the present invention, and together with the description, are intended to describe the principles of the disclosure.

The various aspects and characteristics described in the present description can be applied individually where possible. These individual aspects, for example aspects and characteristics described in the description or in the attached dependent claims, can be the object of divisional applications.

It is understood that any aspect or characteristic that is discovered, during the patenting process, to be already known, shall not be claimed and shall be the object of a disclaimer.

BRIEF DESCRIPTION OF THE DRAWINGS

These and other characteristics of the present invention will become apparent from the following description of some embodiments, given as a non-restrictive example with reference to the attached drawings wherein.

To facilitate comprehension, the same reference numbers have been used, where possible, to identify identical common elements in the drawings. It is understood that elements and characteristics of one embodiment can conveniently be incorporated into other embodiments without further clarifications.

DETAILED DESCRIPTION OF SOME EMBODIMENTS

The embodiments described here concern a method for processing data, of which some particular embodiments will be described below, by way of a non-limiting example.

The various embodiments described in detail below concern a method and apparatus for sterilizing objects, for example blisters containing a plurality of tablets or capsules or pills.

It is clear that the method and the apparatus according to the present invention can be advantageously also used in any other sector, different from the pharmaceutical sector, without departing from the field of protection of the present invention.

Figure 1:
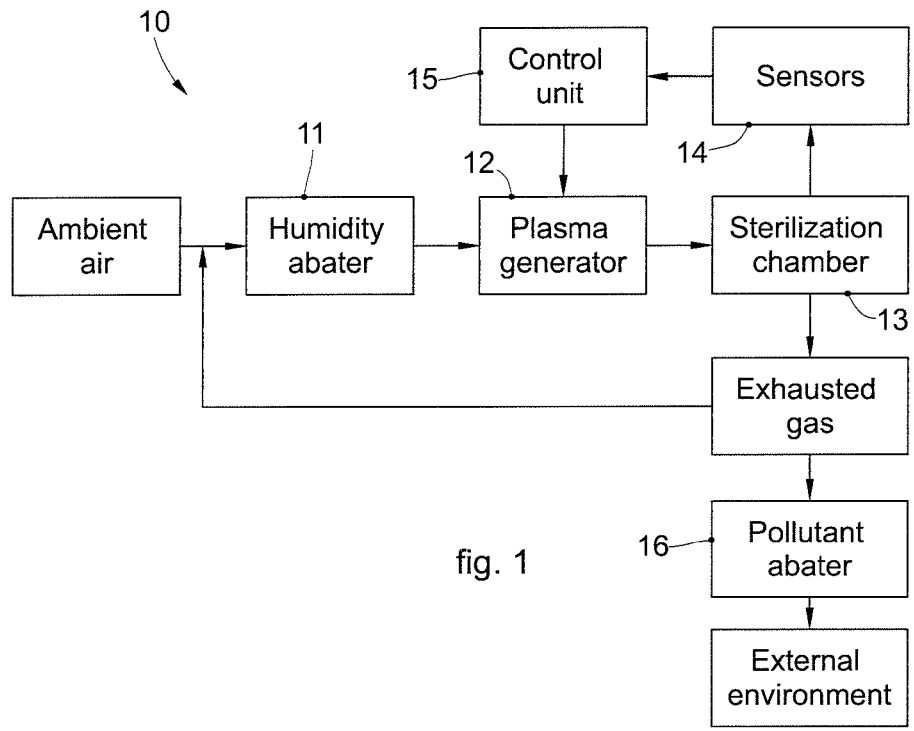
FIG. 1 is a block diagram of an embodiment of an apparatus able to implement a sterilization method using plasma according to the present invention.

With reference to FIG. 1, this shows a block diagram representative of the functioning of a sterilization apparatus according to the present invention, indicated as a whole with reference number 10.

The sterilization apparatus 10 comprises a humidity abatement device 11, of a type known in the state of the art.

The sterilization apparatus 10 also comprises a plasma generator device 12, which will be described in greater detail below with particular reference to FIGS. 3a-3b and 4a-4b, and a sterilization chamber 13 configured to receive the objects to be sterilized.

One or more sensors 14 are disposed in the sterilization chamber 13, of a type known in the state of the art, configured to detect the presence of reactive species, their quantity and the respective chemical composition. For example, the sensors 14 can comprise optical sensors, absorption sensors, etc.

The sensors 14 are operatively connected to a control unit 15, configured to command the adjustment of the plasma generator device 12, based on the information received from the sensors 14.

The sterilization apparatus 10 comprises a pollutant abatement device 16, associated with the sterilization chamber 13 in a suitable position such that it is passed through by the exhausted gaseous components intended to leave the sterilization chamber 13 to be released into the atmosphere.

In one embodiment, the pollutant abatement device 16, of a type known in the state of the art, exerts a mechanical action and comprises one or more filters with apertures of suitable sizes according to the nature of the particles of the polluting substances to be treated.

In another embodiment, the pollutant abatement device 16, of a type known in the state of the art, exerts a chemical action, thanks to which the pollutants interact with suitable reactants able to abate their polluting charge.

The sterilization apparatus 10 also comprises a plurality of pumping members and valve elements, of a type known in the state of the art and not shown, which are suitably disposed on the entry pipes of the gaseous components, and on their exit pipes, into/from the sterilization chamber 13 so as to suitably allow a sealed insulation which hermetically seals the sterilization chamber itself.

Figure 2:
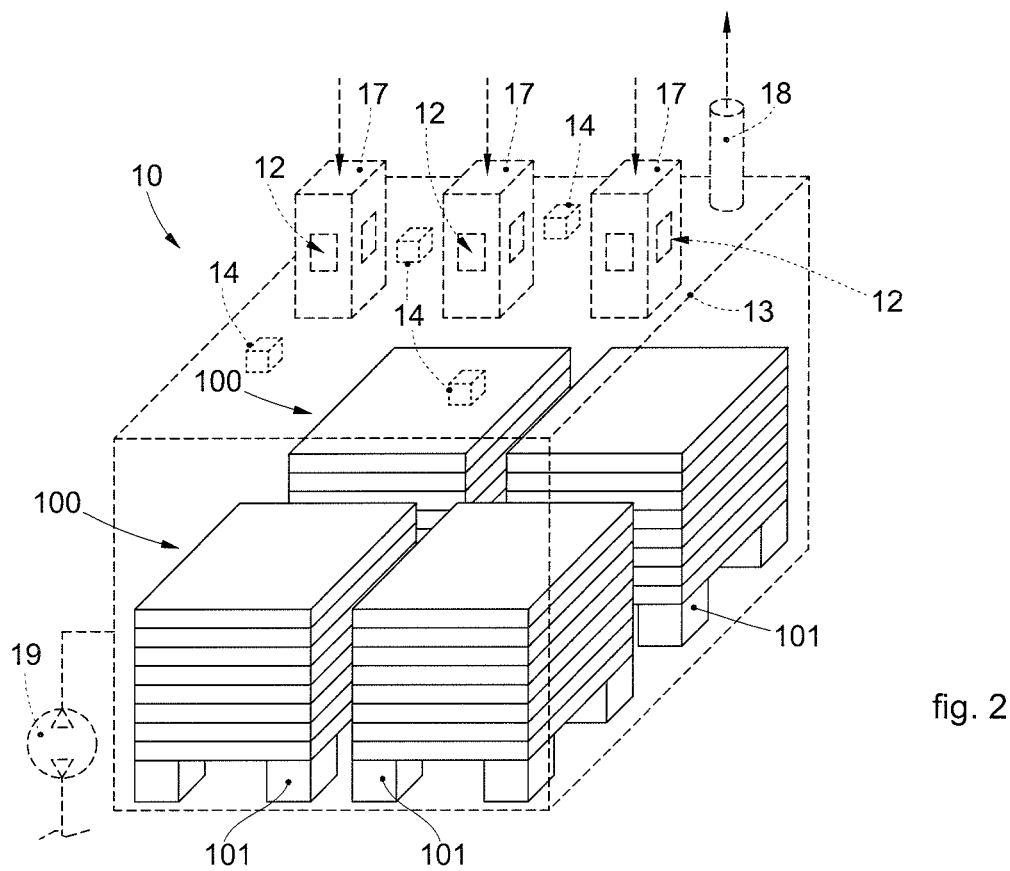
FIG. 2 is a schematic, perspective view of an embodiment of an apparatus able to implement a sterilization method using plasma according to the present invention.

With reference to FIG. 2, an example of a sterilization apparatus 10 is shown in which the sterilization chamber 13 is configured as a large closed compartment. In this embodiment, the sizes of the sterilization chamber 13 are comparable to those of a room, or of a space, for example, of up to a few meters for each side.

It is evident that, in other equivalent embodiments, sterilization chambers 13 with much larger or smaller sizes can be provided, for example comparable to those of a device resting on a laboratory bench.

In the embodiment of FIG. 2, suitable to implement the method according to the present invention on an industrial scale, a plurality of objects 100 are disposed inside the sterilization chamber 13, disposed in order on four pallets 101. For example, the objects 100 can be disposed in an orderly manner on a plurality of levels, above each pallet 101.

In this embodiment, the sterilization chamber 13 comprises access means that can be hermetically sealed, not shown, which are suitably sized so as to allow access to the sterilization chamber 13 to loading vehicles suitable to transport the pallets 101.

The sterilization apparatus 10 comprises at least one feed pipe 17, configured to introduce gas into the sterilization chamber 13.

By way of a non-limiting example, the embodiment shown provides three feed pipes 17 with a square section (FIG. 3a), disposed in parallel.

It is evident that other equivalent embodiments can provide a single feed pipe 17, or a plurality of feed pipes 17, in a number different from three.

According to an alternative embodiment, the feed pipes 17 can be disposed according to a parallel configuration, in which a single gas collector is provided, from which the various feed pipes 17 depart.

In other equivalent embodiments, the feed pipes 17 can have a cross-section other than square, for example circular.

According to some embodiments, in proximity to the connection between the feed pipes 17 and the sterilization chamber 13 suitable valve elements are provided, of a type known in the state of the art and not shown, able to selectively separate the respective feed pipe 17 from the sterilization chamber 13.

A respective plasma generator device 12 is associated with each feed pipe 17 in proximity to the sterilization chamber 13, which have been schematized with dashed rectangles in FIG. 2.

According to embodiments provided here, the sterilization apparatus 10 comprises an exit pipe 18 configured to release the exhausted gases from the sterilization chamber 13, which can be selectively put in flow connection with the latter.

According to embodiments described here, the sterilization apparatus 10 comprises a vacuum pump 19, of a type known in the state of the art, suitable to bring the sterilization chamber 13 into a condition of depression, or vacuum condition, that is, to a lower pressure than atmospheric pressure, according to modes known in the state of the art.

The plasma generator device 12 comprises a plurality of electrodes 20. For example, each plasma generator device 12 comprises four electrodes 20.

In one embodiment, each electrode 20 is disposed on a respective wall 17A, 17B, 17C, 17D of the feed pipe 17.

Each electrode 20 is connected to electric supply means, according to modes known in the state of the art, which apply a certain voltage to generate a suitable electric field.

In a preferred embodiment, the electrodes 20 are of the type described in the scientific publication by G. Neretti et al. titled "*Geometry optimization of linear and annular plasma synthetic jet actuators*" in the *Journal of Physics D: Appl. Phys.* 50 (2017) 015210 (9pp), to be considered here incorporated in its entirety as reference.

Figure 4A:
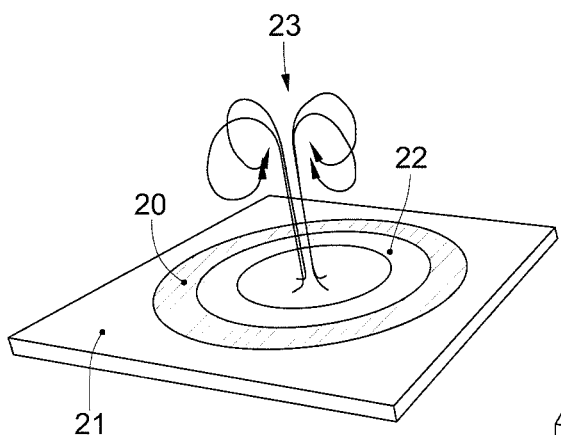
FIGS. 4a and 4b are variant embodiments of an enlarged detail comprised in the apparatus of FIG. 2.
Figure 4B:
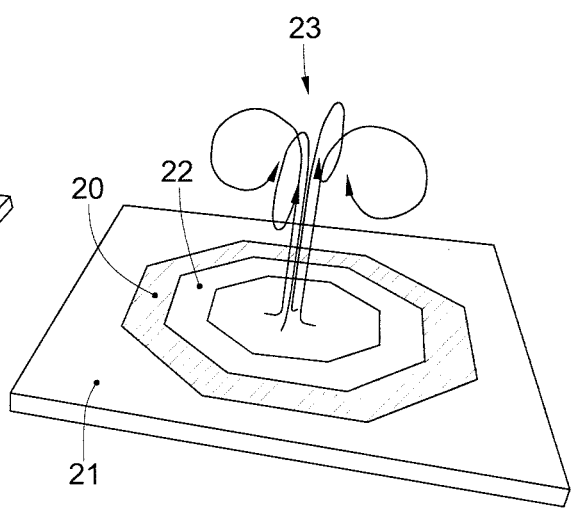

Two variant embodiments of an electrode 20 according to embodiments provided according to the present invention, respectively with reference to FIGS. 4a and 4b are described below.

FIG. 4a shows an electrode 20 disposed on a plate 21 of dielectric material, for example made of a material selected from the polychlorinated biphenyl (PCB) family, with a thickness for example of about 1.6 mm. The electrode 20 is configured as an annular element made of copper with a thickness of about 35 microns, an internal diameter of about 30 mm and an amplitude of about 5 mm.

FIG. 4b shows an electrode 20 disposed on a plate 21 of dielectric material, for example made of polyvinyl chloride (PVC) or glass. The electrode 20 is configured as an octagonal shaped element made of copper with a thickness of about 35 microns, an amplitude of about 5 mm, and an internal length of each side of about 12 mm.

Figure 3A:
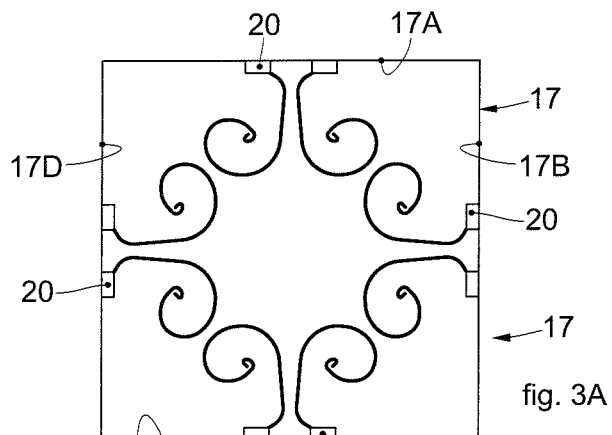
FIGS. 3a and 3b are schematic, section views of a portion of the apparatus of FIG. 2.
Figure 3B:
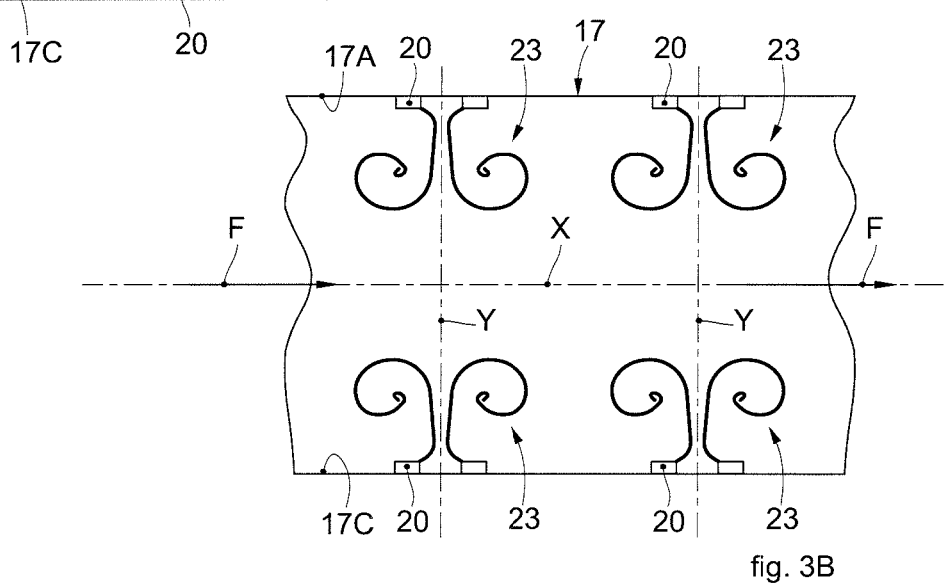

It should be noted that in both these configurations the electrode 20 is shaped so as to define a configuration of symmetry with respect to a central axis of symmetry Y (shown in FIGS. 3a and 3b).

Applying a differential voltage between the electrode 20 and the lower face of the plate 21 allows to generate a plasma, according to modes known in the state of the art, which develops, inside the electrode 20, on an area that follows the shape of the electrode, which has been filled with dashes in the drawings and is indicated with reference number 22.

As is known, the plasma 22 generates a mixture of reactive species which move away from the electrode 20 according to a jet which is schematized with the combination of four curved arrows and is indicated as a whole with reference number 23.

Thanks to the peculiar geometry of the electrodes 20 described above, the jet 23 is oriented so as to develop, at least partly, coaxially with the central axis of symmetry Y. In particular, the jet 23 is directed away from the electrode 20 toward an axis of longitudinal development X of the feed pipe 17, in a direction substantially perpendicular to the latter.

The sterilization method using plasma according to the present invention is described below.

Initially, the method provides to introduce the objects 100 in the sterilization chamber 13, which, after having been hermetically closed, is put in a vacuum condition.

Subsequently, the sterilization method using plasma provides to activate the plasma generator device 12. The activation of the latter allows to generate one or more gaseous compounds comprising a mixture of reactive oxygen species (ROS), and reactive nitrogen species (RNS). In particular, the reactive oxygen species and the reactive nitrogen species generated by the plasma comprise ozone ($O_3$), dinitrogen oxide ($N_2O$), nitrogen pentoxide ($N_2O_5$) and nitric acid ($HNO_3$).

According to embodiments provided here, the activation of the plasma generator device 12 also allows the generation of free ions, in stable form, which remain stable long enough to reach the sterilization chamber 13. It has been observed, in particular, that the free ions comprise particles with a positive charge, such as for example oxonium ($H_3O^+$). Experimental tests have allowed to verify that the presence of these positively charged particles allows to increase the effectiveness of the sterilizing action of the plasma. In other words, if—in addition to the gaseous compounds comprising the mixture of reactive oxygen species and reactive nitrogen species—the free ions in stable form mentioned above are present, it is possible to sterilize the same quantity of objects 100 in a shorter time, with the same effectiveness of the sterilization action.

Figure 5:
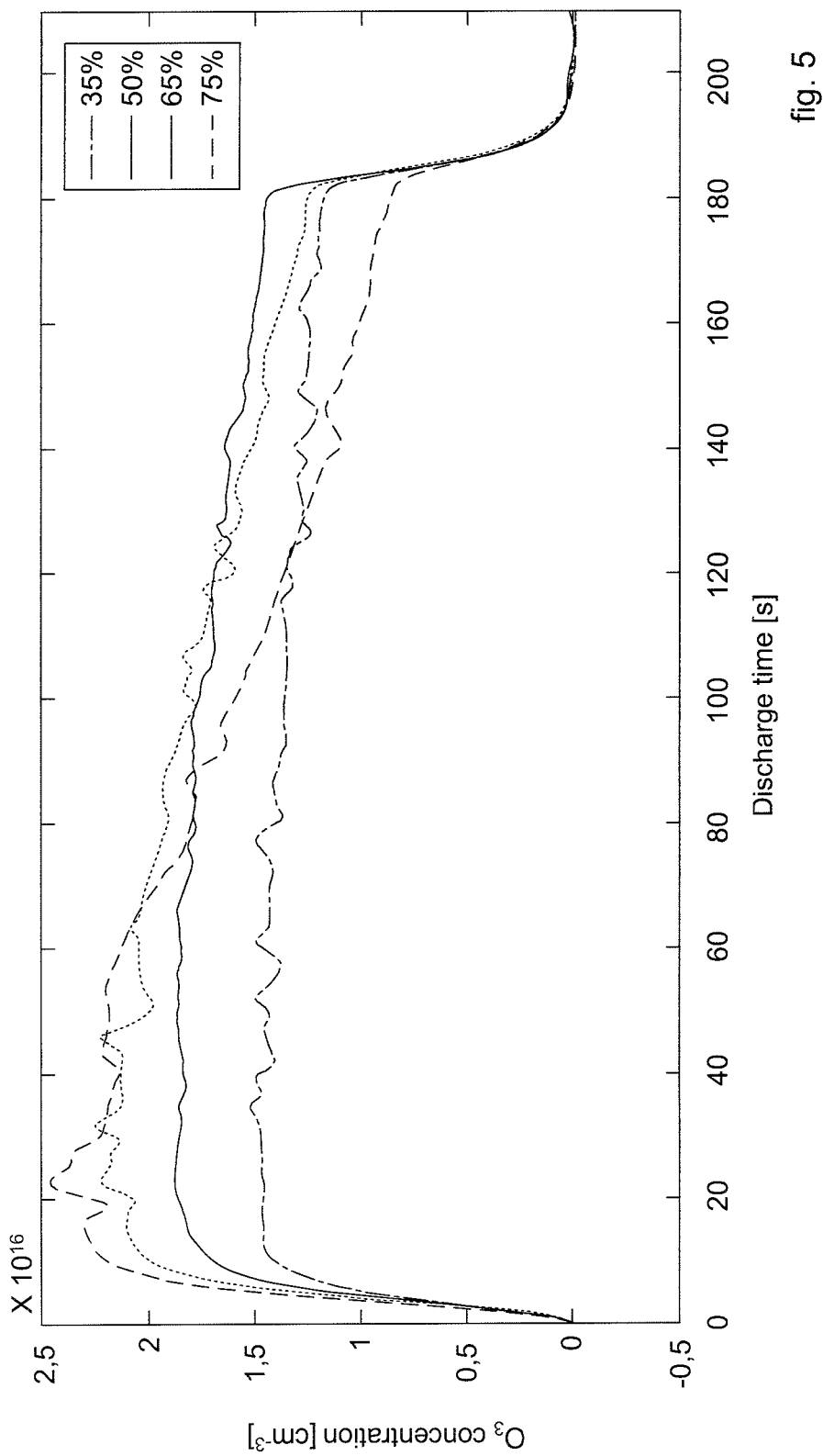
FIG. 5 is a graph showing the trend of ozone concentration in the sterilization chamber comprised in the apparatus of FIG. 2 as a function of the time of application of the electric discharge to the electrodes.

With reference to FIG. 5, the graph shows the trend of the ozone concentration as a function of the discharge time, for four different values of activation time of the plasma generator device 12 (respectively at 35%, 50%, 65% and 75%). The curves were respectively obtained by electrically powering the electrode 20 for a fraction of time during which the plasma generator device 12 is active equal respectively to the percentage value indicated.

Experimental tests show that the 50% curve is the best compromise that allows to obtain an optimal ozone concentration.

It is noted that the experimental tests performed have yielded excellent results. In fact, the ozone concentration values remain approximately equal to, or higher than, $1.5 \times 10^{16}$ cm$^{-3}$ in the period from 10s to 180s of the discharge time, for the 50% curve.

These concentration values are advantageously much higher, from three to ten times, than the typical concentrations of other reactive species generated by the plasma generator device 12.

The method then provides to feed air along the feed pipe 17, which is put in communication with the sterilization chamber 13.

According to a preferred embodiment, it is provided to feed dehumidified air along the feed pipe 17.

In one embodiment, the dehumidified air is obtained starting from ambient air that passes through the humidity abatement device 11, disposed upstream of the feed pipe 17.

In one embodiment, the dehumidified air is obtained from pressurized containers (for example cylinders) of synthetic air, directly connected to the feed pipe 17.

The dehumidified air passes through the feed pipe 17 in the direction indicated by arrows F in FIG. 3b, that is, parallel to the longitudinal axis of development X.

The flow of dehumidified air defines the carrier fluid which conveys the gaseous compounds, that is, the reactive species and possibly the free ions mentioned above, toward the sterilization chamber 13. It has been observed that the configuration described above, in which the jets 23 are oriented substantially orthogonal with respect to the flow of dehumidified air, is advantageous as it allows to optimize the electro-hydrodynamic effect so as to increase the quantity of reactive species produced in the unit of time.

According to some embodiments, the method provides to maintain flow communication between the feed pipe 17 and the sterilization chamber 13 for a determinate period of time, such as to allow the gaseous compounds to enter the sterilization chamber 13 and to be distributed homogeneously in the latter. In one embodiment, the determinate period of time is, for example, equal to or greater than the time during which the plasma generator device 12 remains active. In other words, the determinate period of time has to be sufficient to allow the substantial saturation of the sterilization chamber with the gaseous compounds mentioned above.

According to embodiments of the method according to the present invention, it is provided to control, by means of the control unit 15, the electric power used to produce the plasma as a function of the composition and/or the quantity of reactive species present in the sterilization chamber 13, detected by the sensors 14.

Experimental tests have allowed to identify optimal values of the electric power with which to power the electrodes 20 during the activation step of the plasma generator device 12 in order to maximize the quantity of reactive species 12 produced in the unit of time.

In one embodiment, the optimum values provide to subject each electrode 20 to an electric field which is comprised between $10^5$ and $10^8$ volts/meter, preferably comprised between $10^6$ and $10^7$ volts/meter.

According to some embodiments, the electric field values can be obtained by applying to the electrodes 20 voltage values comprised between 1 V and 100 kV and frequencies comprised between 1 Hz and 20 MHz.

Once the activation step of the plasma generator device 12 has ended, it is provided to interrupt the electric power supply of the electrodes 20, thus deactivating the plasma generator device 12.

The deactivation step of the plasma generator device 12 provides to interrupt the flow connection between the feed pipe 17 and the sterilization chamber 13 by driving suitable valve elements and subsequently waiting for a deposition time during which the mixture of reactive species, and possibly the free ions, is/are deposited on the objects 100 to be sterilized to perform their sterilizing function. Once the deposition time has elapsed, the method provides a step of removing the exhausted gases in order to remove the reactive species and the possible free ions still present in the sterilization chamber 13, again returned to a vacuum condition by means of the vacuum pump 19.

In one embodiment, the step of removing the exhausted gases provides to reintroduce the gases into the feed pipe 17, upstream of the plasma generator device 12 (FIG. 1).

In another embodiment, alternative to or actuated together with the previous one, the step of removing the exhausted gases provides to release the gases into the atmosphere by means of the exit pipe 18, after performing suitable treatments to reduce, or even eliminate, possible polluting substances in order to respect the legal limits provided (FIG. 1).

Finally, before the operator removes the sterilized objects 100, the method provides to bring the sterilization chamber 13 back to atmospheric pressure.

It is clear that modifications and/or additions of steps or parts may be made to the sterilization method and apparatus as described heretofore, without departing from the field and scope of the present invention.

It is also clear that, although the present invention has been described with reference to some specific examples, a person of skill in the art shall certainly be able to achieve many other equivalent forms of sterilization method and apparatus, having the characteristics as set forth in the claims and hence all coming within the field of protection defined thereby.

The invention claimed is:

1. A sterilization method using plasma for sterilizing objects, the method comprising the steps of:
introducing the objects to be sterilized into a sterilization chamber defined by an environment hermetically separated from the outside,
bringing said sterilization chamber to pressures lower than atmospheric pressure by means of a vacuum pump,
activating a plasma generator device disposed on at least one feed pipe leading to said sterilization chamber so that one or more gaseous compounds comprising a mixture of reactive oxygen species (ROS) and of reactive nitrogen species (RNS), and optionally free ions with positive charge, are generated by the plasma generator device and conveyed to said sterilization chamber, feeding air along said at least one feed pipe and putting the latter in communication with said sterilization chamber for a determinate period of time to allow said gaseous compounds to enter said sterilization chamber and spread in a substantially homogeneous way therein, said period of time being equal to or more than the activation time of said plasma generator device, said air being a carrier fluid which conveys the gaseous compounds into said sterilization chamber, controlling, by means of a control unit, the electric power used to produce the plasma during said activation step of the plasma generator device as a function of the composition and/or the quantity of reactive species present in said sterilization chamber, detected by suitable sensor means, characterized in that said at least one feed pipe has a square section, in that said plasma generator device comprises four electrodes on the walls of said at least one feed pipe, according to a configuration wherein each of the four electrodes are oriented on a respective wall of the at least one feed pipe such that the central axis of symmetry of each of the four electrodes is arranged on the square section such that each electrode opposes another of the electrodes, and in that each of said electrodes has a circular or polygonal shape defining a configuration of symmetry with respect to a central axis of symmetry (Y).

2. The sterilization method of claim 1, characterized in that during said activation step of said plasma generator device, in correspondence with each of said electrodes, a jet of said mixture of reactive species is generated which is oriented so as to develop, at least partly, coaxially to said central axis of symmetry (Y), being directed away from said electrode, toward a longitudinal axis of development (X) of said at least one feed pipe, in a direction perpendicular to the latter, and in that each of said electrodes is disposed on a dielectric material.

3. The sterilization method of claim 1, characterized in that during said activation step, each of said electrodes is subjected to an electric field, regulated during the control step, which is comprised between $10^5$ and $10^8$ volts/meter.

4. The sterilization method of claim 1, characterized in that, once said activation step of said plasma generator device is terminated, a deactivation step of the latter is provided, in which it is provided to interrupt the electric power of said electrodes.

5. The sterilization method of claim 4, characterized in that said deactivation step of said plasma generator device provides to: interrupt the flow connection between said at least one feed pipe and said sterilization chamber and, subsequently, to wait for a deposition time during which the mixture of reactive species is deposited on the objects to be sterilized in order to perform their sterilizing function, and once said deposition time has elapsed, to remove the exhausted gases in order to remove the reactive species present in said sterilization chamber, again returned to pressures lower than atmospheric pressure.

6. The sterilization method of claim 5, characterized in that during said step of removing the exhausted gases it is provided to reintroduce gaseous compounds comprising said mixture of reactive species, into said at least one feed pipe, or it is provided to process the gaseous compounds so as to reduce, or even eliminate, possible pollutant substances, before re-introducing them into the atmosphere.

7. The sterilization method of claim 5, characterized in that, after said step of removing the exhausted gases, it is provided to return said sterilization chamber to atmospheric pressure, before an operator removes the sterilized objects.

8. An apparatus for sterilizing objects, in particular loose objects or packaged in blisters or pouches or sachets, suitable to actuate a sterilization method using plasma as in any one of the previous claims, and comprising: a sterilization chamber for the objects configured to be hermetically separated from the outside, a feed pipe to convey air toward said sterilization chamber, a plasma generator device (12) to generate one or more gaseous compounds comprising a mixture of reactive oxygen and nitrogen species and disposed in said feed pipe, pumping members and valve units configured to control the flow of air and gaseous compounds to and from said sterilization chamber, sensor means configured to detect a quantity and/or composition of said reactive oxygen and nitrogen species present inside said sterilization chamber, and a control unit (15) configured to control at least the electric power used to produce the plasma during said activation step of the plasma generator device, said apparatus being characterized in that said feed pipe has a square section, in that said plasma generator device comprises four electrodes on the walls of said feed pipe, each electrode is disposed on a respective wall of said feed pipe and is oriented such that the central axis of symmetry of each of the four electrodes is arranged on the square section such that each electrode opposes another of the electrodes; and in that each of said electrodes has a circular or polygonal shape defining a configuration of symmetry with respect to a central axis of symmetry (Y).

* * * * *